United States Patent
Cook et al.

(10) Patent No.: US 9,763,453 B2
(45) Date of Patent: Sep. 19, 2017

(54) ANTIMICROBIAL COATING FOR INHIBITION OF BACTERIAL ADHESION AND BIOFILM FORMATION

(71) Applicant: Bacterin International, Inc., Belgrade, MT (US)

(72) Inventors: Guy S. Cook, Bozeman, MT (US); Matt R. Trebella, Bozeman, MT (US)

(73) Assignee: Bacterin International, Inc., Belgrade, MT (US)

( * ) Notice: Subject to any disclaimer, the term of this patent is extended or adjusted under 35 U.S.C. 154(b) by 0 days.

(21) Appl. No.: 14/268,473

(22) Filed: May 2, 2014

(65) Prior Publication Data

US 2015/0010715 A1    Jan. 8, 2015

Related U.S. Application Data

(62) Division of application No. 10/891,885, filed on Jul. 15, 2004, now abandoned.

(60) Provisional application No. 60/566,576, filed on Apr. 29, 2004.

(51) Int. Cl.
| | | |
|---|---|---|
| A01N 25/10 | (2006.01) |
| A01N 59/16 | (2006.01) |
| B05D 3/10 | (2006.01) |
| A61L 27/34 | (2006.01) |
| A61L 27/54 | (2006.01) |
| A61L 29/08 | (2006.01) |
| A61L 29/16 | (2006.01) |
| A61L 31/10 | (2006.01) |
| A61L 31/16 | (2006.01) |
| B05D 3/14 | (2006.01) |
| C09D 5/14 | (2006.01) |

(52) U.S. Cl.
CPC .............. *A01N 59/16* (2013.01); *A01N 25/10* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *B05D 3/104* (2013.01); *B05D 3/142* (2013.01); *C09D 5/14* (2013.01); *A61L 2300/104* (2013.01); *A61L 2300/406* (2013.01); *A61L 2300/606* (2013.01)

(58) Field of Classification Search
None
See application file for complete search history.

(56) References Cited

U.S. PATENT DOCUMENTS

| | | |
|---|---|---|
| 3,886,094 A | 5/1975 | Pilato et al. |
| 4,446,124 A | 5/1984 | Fox, Jr. et al. |
| 4,849,223 A | 7/1989 | Pratt et al. |
| 4,920,158 A * | 4/1990 | Murray et al. ................ 523/111 |
| 5,219,325 A | 6/1993 | Hennink et al. |
| 5,260,066 A | 11/1993 | Wood et al. |
| 5,496,877 A * | 3/1996 | Aumueller et al. .......... 524/246 |
| 5,688,855 A | 11/1997 | Stoy et al. |
| 5,810,755 A | 9/1998 | LeVeen et al. |
| 5,879,757 A | 3/1999 | Gutowski et al. |
| 5,981,826 A | 11/1999 | Ku et al. |
| 6,139,856 A | 10/2000 | Kaminska et al. |
| 6,159,531 A * | 12/2000 | Dang et al. .................. 427/2.24 |
| 6,238,691 B1 | 5/2001 | Huang |
| 6,428,903 B1 | 8/2002 | Callegaro |
| 6,444,750 B1 | 9/2002 | Touhsaent |
| 6,468,521 B1 | 10/2002 | Pedersen et al. |
| 6,716,895 B1 | 4/2004 | Terry |
| 6,861,067 B2 | 3/2005 | McGhee et al. |
| 7,863,264 B2 | 1/2011 | Vange et al. |
| 2001/0026810 A1 | 10/2001 | McGhee et al. |
| 2004/0116551 A1 | 6/2004 | Terry |

FOREIGN PATENT DOCUMENTS

| | | |
|---|---|---|
| JP | S61190536 A | 8/1986 |
| JP | S62277330 A | 12/1987 |
| JP | H02268103 A | 11/1990 |
| JP | H04220258 A | 8/1992 |
| JP | H09508157 A | 8/1997 |
| JP | 2000063218 A | 2/2000 |
| JP | 2001502581 A | 2/2001 |
| JP | 2001525344 A | 12/2001 |
| JP | 2002539895 A | 11/2002 |
| JP | 2003529630 A | 10/2003 |
| JP | 2004509907 A | 4/2004 |
| JP | 2004532815 A | 10/2004 |
| WO | 9623428 A | 8/1996 |
| WO | WO 9729160 A1 * | 8/1997 |
| WO | WO03047636 A2 | 6/2003 |

(Continued)

OTHER PUBLICATIONS

Owen et al., J. Adhesion Sci. Technol., 1994, 8(10), 1063-1075.*
The European Communication for European Application No. 05744133.9-1454, mailed Aug. 7, 2013.
Nesbitt, et al., "Solubility Studies of Silver Sulfonamides," J. Pharm. Sci., 67(7): 1012-1017 (1978).
Gilbert et al., IEE Digest, 1995, 170, pp. 1-5.
The Merck Index, 1984, Windholz ed., pp. 1221-1224 and 1275.
Smith & Nephew, Flamazine Technical Data Sheet, http://wound.smith-nephew.com, obtained via waybackmachine www.web.archive.org. on Sep. 1, 2009, available online on Sep. 7, 2003.
Akiyama et al., Journal of Antimicrobial Chemotherapy, 1998, 42, 629-634.

(Continued)

*Primary Examiner* — Abigail Fisher
(74) *Attorney, Agent, or Firm* — Kinney & Lange, P.A.

(57) ABSTRACT

The present invention provides antimicrobial coatings for coating substrate surfaces, particularly medical devices, for preventing bacterial adhesion and biofilm formation by inhibiting microbial growth and proliferation on the coating surface. The antimicrobial coatings are composed of a hydrogel and a bioactive agent including a substantially water-insoluble antimicrobial metallic material that is solubilized within the coating. Antimicrobial coating formulations for obtaining such coatings, and coating methods are also described.

13 Claims, 4 Drawing Sheets

(56) References Cited

FOREIGN PATENT DOCUMENTS

| WO | 03093357 A1 | 11/2003 |
| WO | 2004028255 A1 | 4/2004 |
| WO | 2005056070 A1 | 6/2005 |

OTHER PUBLICATIONS

Japanese Office Action for Japanese Patent Application No. 2007-511086, dated Aug. 16, 2011, 4 pages.
Elsome Am, Hamilton-Miller JMT, Brumfill W, Noble WC., "Antimicrobial activities in vitro and in vivo of transition element complexes containing gold (I) and osmium (VI)." J. Antimicrobial Chemotherapy (1996); 37(5): 911-918.
Faundez G, Troncoso M, Navarrete, P, Figueroa G. "Antimicrobial activity of copper surfaces against suspensions of *Salmonella enterica* and *Camplyobacter Jejuni*." BMC Microbiology (2004); 4:19.
Fricker SP., "Medicinal chemistry and pharmacology of gold compounds." Transition Met Chem (1996); 21: 377-383.
Balogh L, Swanson DR, Tomalia DA, Hagnauer GL, McManus AT. "Dendrimer—Silver complexes and nanocomposities as antimicrobial agents." Nano Letters (2001); 1: 18-21.
Drury JL, Mooney DJ. "Hydrogels for tissue engineering: scaffold design variables and applications." Biomaterials (2003); 24: 4337-4351.
Watanable J., Kiritoshi Y, Nam K, Isihara K., (2004), "Hydrogels" In Wnek GE, Bowlin GL (Eds.), Encyclopedia of Biomaterials and Biomedical Engineering: vol. 1: A-K. (pp. 790-801). New York, New York: Marcel Dekker Incorporated.
Weinberg, ED. "The mutual effects of antimicrobial compounds and metallic cations." Bacteriol Rev. (1957); 21(1) 46-68.

\* cited by examiner

ANTIMICROBIAL COATING FOR INHIBITION OF BACTERIAL ADHESION AND BIOFILM FORMATION

CROSS-REFERENCE TO RELATED APPLICATION(S)

This application is a divisional of U.S. application Ser. No. 10/891,885, filed on Jul. 15, 2004, which claims the benefit of U.S. Provisional Application No. 60/566,576, filed on Apr. 29, 2004. The entire teachings of the above applications are incorporated herein by reference.

FIELD OF THE INVENTION

The present invention relates to an antimicrobial coating for coating a substrate surface, particularly medical devices that are likely to become contaminated or have become contaminated with microorganisms as a result of bacterial adhesion and proliferation and methods for preventing biofilm formation by inhibiting microbial growth and proliferation on the surface of medical devices.

BACKGROUND OF THE INVENTION

Colonization of bacteria on the surfaces of medical devices and healthcare products, particularly in implanted devices, result in serious patient problems, including the need to remove and/or replace the implanted device and to vigorously treat secondary infection conditions. Considerable efforts, therefore, have been directed toward preventing such colonization by the use of antimicrobial agents, such as antibiotics, that are bound to the surface of the materials used in such medical devices. The focus of prior attempts has been to produce a sufficient bacteriostatic or bactericidal action to prevent microbial colonization on the device surface.

As a defense against antimicrobial agents that would affect their survival and proliferation, many surface adhered microorganisms form a defense layer comprising a mucopolysaccharide film called biofilm. Formation of biofilms on the surface of medical devices can be detrimental to the integrity of the medical device, present health risks, and prevent sufficient flow through the lumens of medical devices. Furthermore, biofilms formed on the device surface recruit non-adhered or "sessile" microorganisms from the device environment, such as urine or blood, and enable their propagation. Particulate biofilm matter that periodically detach from the surface of a medical device or healthcare product, for example, therefore provide, a continued source of pathologically infectious microorganisms that can contaminate the physiological environment in which the medical device or healthcare product is in contact with, that can result in serious secondary infections in patients.

Although coating or cleaning medical devices with antimicrobial agents, such as antibiotics or antiseptics, can be effective in killing or inhibiting growth of free-floating or "planktonic" organisms not adhered to the device surface, such antimicrobial agents are generally much less active against the microorganisms that are deeply embedded within the biofilm due to their inability to penetrate the biofilm. The failure of the antimicrobial agents to sufficiently remove the microorganisms is therefore largely due to the protective effect of the biofilm which prevents diffusion of antimicrobial deep into the biofilm layer to eliminate the microorganisms proliferating within therein.

Biofilm associated problems experienced with implantable medical devices such as catheters, particularly catheters designed for urinary tract infections, pose a significant risk for catheterized patients of acquiring secondary infection such as nosocomial infection in a hospital environment. Such infections can result in prolonged hospital stay, administration of additional antibiotics, and increased cost of post-operative hospital care. In biofilm mediated urinary-tract infections, bacteria are believed to gain access to the catheterized bladder either by migration from the collection bag, the catheter by adhering to and proliferating on the material constituting the catheter material, or by ascending the periurethral space outside the catheter. Although, the use of antimicrobially coated catheters wherein antibiotic agents or antimicrobial compounds are dispersed within the coating have been reported to reduce the incidence of catheter associated bacteriuria, such coatings have proven to be largely ineffective in preventing bacterial adhesion and biofilm formation on the catheter surface for extended periods, and therefore do not sufficiently retard the onset of bacterial infection.

The use of silver compounds in antimicrobial coatings for medical devices is known in the art. The antiseptic activity of silver compounds is a well-known property that has been utilized for many years in topical formulations. Silver is known to possess antibacterial properties and is used topically either as a metal or as silver salts due to their ability to generate bactericidal amounts of silver ions ($Ag^+$), in which in this bioactive species, is released to the contacting environment. The bactericidal and fungistatic effect of the silver ion have been extensively utilized clinically; for example, silver nitrate, which is readily soluble (highly ionizable) in water, at concentrations of 0.5-1% exhibits disinfectant properties and is used for preventing infections in burns or for prophylaxis of neonatal conjunctivitis. Silver nitrate however, can cause toxic side effects at these concentrations, and does cause discoloration of the skin (Argyria).

A specific advantage in using the silver ion as antibacterial agent is the inability of bacteria to acquire tolerance to the silver ion, which is in contrast to many types of antibiotics. Unlike antibiotics, the potential for bacterial to become silver ion resistant is therefore quite low. However, it is also recognized that silver compounds capable of providing bactericidal levels of silver ion have reduced photostability, and tend to discolor in presence of light and or heat as a result of photoreduction of $Ag^+$ ion to metallic silver. Furthermore, commonly used terminal sterilization processes such as gamma or e-beam radiation of coatings or formulations containing such silver compounds results in discoloration and loss of activity in such materials, whether it is in the form a cream, gel or as a coating on a medical device. Silver compounds that have extremely low solubility in aqueous solutions such as silver iodide ($K_{sp} \sim 10^{-18}$) and silver sulfide ($K_{sp} \sim 10^{-52}$) on the other hand, are relatively more photostable but poorly ionized, and hence cannot provide bactericidal levels of silver ions into the contacting environment. They are therefore, either weakly antibacterial (bacteriostatic), or inert.

Silver compounds with relatively low aqueous solubilities but sufficient ionization such as silver oxide ($Ag_2O$) and silver chloride ($AgCl$)($K_{sp} 10^{-8}$ to $10^{-9}$) are weakly antibacterial and have been used in antimicrobial coatings. However, they are incorporated as micronized particles suspended within the coating which effectively reduces the effective concentration of $Ag^+$ ions released from such coatings, resulting in shorter coating efficiency and greater tendency to fail in bacterially rich or growth promoting environments. Silver sulfadiazine (AgSD), a substantially water insoluble compound ($K_{sp} \sim 10^{-9}$) has a combination of a weakly antibacterial sulfadiazine molecule that is complexed with silver. In contrast to silver nitrate, the solubility of the silver sulfadiazine complex is relatively low, and hence both silver ion and sulfadiazine are present only in low concentrations in aqueous solutions. The antibacterial effect of AgSD in topical formulations may therefore, persist over a longer period of time before being washed out at topically treated wound sites. AgSD is therefore, used in the treatment of wounds, particularly for burns, under the trademarks Silvadene® and Flamazine®. The substantially low water solubility of AgSD has however, limited its use in antimicrobial coatings, particularly in thin coatings for medical devices. Attempts to incorporate AgSD into antimicrobial coatings involve dispersion AgSD as micronized particles within relatively hydrophilic polymeric coating materials such as polyethyleneglycol (PEG) and polyvinylalcohol (PVA) which significantly limits the ability to obtain high AgSD concentrations in thin coatings, without compromising coating integrity and mechanical properties. European patent application EP 83305570 discloses a polyvinylpyrollidone hydrogel containing micronized AgSD and cross-linked by e-beam radiation used as an absorbent wound dressing . . . . Such hydrogel absorbent materials are however, not suitable for coating of medical devices in which high loading of particulate AgSD is not achievable. Furthermore, the antimicrobial efficacy of such coatings are relatively poor because of the relatively low concentrations of silver ($Ag^+$) ions in the coating, and such coatings therefore require additional water-soluble antimicrobial compounds, such as chlorhexidine to provide bactericidal levels of antimicrobial agents in the contacting environment. Such increased elution of the non-silver agent however, is likely to adversely affect the duration of coating efficacy, since the coating becomes depleted of the soluble agent in a relatively short period of time. Such antimicrobial coatings therefore, are not optimal for medical devices that remain implanted in the patient for longer periods of time (several days to weeks).

SUMMARY OF THE INVENTION

The present invention is based upon the realization that a substantially water-insoluble antimicrobial material can be incorporated into a hydrophilic polymeric coating in a substantially "solubilized" form wherein the water insoluble antimicrobial material is dispersed homogeneously in a three dimensional hydrogel network gel, formed by a hydrophilic polymer in a substantially homogenous manner, thereby enabling incorporation of high concentrations of a bacteriostatic or bactericidal material in relatively thin coatings, and resulting in increased coating antimicrobial efficacy for extended periods. The coatings of the invention, therefore, inhibit bacterial adhesion and biofilm formation on coated surfaces such as medical devices and healthcare products.

The present invention concerns an antimicrobial coating comprising a cross-linked polymeric material comprising a biologically active or "bioactive" agent and at least one substantially water-insoluble antimicrobial metallic compound maintained in a substantially "solubilized" form within the coating that inhibits bacterial adhesion and proliferation on the coating surface, thereby inhibiting the formation of biofilm. It has been surprisingly found that maintaining the water-insoluble antimicrobial metallic compound in a solubilized form within the hydrogel coating imparts substantially high coating antimicrobial efficacy that is maintained over an extended duration of time relative to hydrogel coatings within which the water-insoluble antimicrobial metallic compound is dispersed as micronized heterogeneous particles.

In one aspect, the present invention relates to an antimicrobial coating on a substrate surface, including surface of a medical device or healthcare product, comprising a hydrogel layer and a substantially water-insoluble antimicrobial metallic compound that is maintained in a substantially "solubilized" form within the coating, that inhibits bacterial adhesion and biofilm formation on the coating surface. In particular, the present invention relates to hydrogel coating comprising a hydrophilic polymer at least a portion of which is crosslinked to form a hydrophilic 3-dimensional (3-D) network within which a substantially water insoluble silver compound is dispersed homogeneously within the coating in a substantially solubilized form.

In another aspect, the present invention provides an antimicrobial coating wherein substantially water-insoluble, poorly ionizing (weakly active) silver compounds or silver complexes are rendered more active in a sustained manner over a longer duration of time by maintaining them in a homogeneously dispersed, solubilized form within the coating.

In a further aspect, the present invention provides a coating formulation comprising a hydrophilic polymeric material and a substantially water-insoluble metallic antimicrobial compound that is dispersed in a substantially homogenous phase in the coating formulation complex structure rendering silver ions stable against loss of the antiseptic activity and against darkening due to reduction of the silver ions or the formation of darkly stained sparingly or insoluble silver compounds.

In yet another aspect, the present invention provides principles and methods of introducing the silver compositions stabilized against the effect of light into catheters, guide-wires, wound drains, needle-less connectors, or similar medical devices or instruments.

In a further aspect the invention provides coating compositions and coating methods for coating substrate materials, particularly medical devices, and evaluation of coating biological activity e including antimicrobial efficacy, and inhibition of bacterial adhesion and biofilm formation.

BRIEF DESCRIPTION OF THE DRAWINGS

FIG. 1A is an image of a substrate coated with micronized AgSD in suspension. FIG. 1B is an image of a substrate coated with AgSD in solution. The coating in FIG. 1B is translucent in appearance.

FIG. 2A is a graph of a static model elution. FIG. 2B is a graph of a dynamic model elution. The vertical axes represent concentration in micrograms per milliliter (µg/mL). The horizontal axes represent time in hours.

FIG. 3 is a graph showing AgSD elution profiles of several crosslinked coating compositions comprising solubilized AgSD and a hydrophobic coating composition comprising micronized AgSD. The vertical axis represents percent AgSD released from the coating. The horizontal axis represents time in hours. Crosslink density is represented by concentration of crosslinking agent.

FIG. 4A is an image of an uncoated polycarbonate outlet housing. FIG. 4B is an image of a coated polycarbonate outlet housing.

DETAILED DESCRIPTION OF THE INVENTION

Figure 1A:
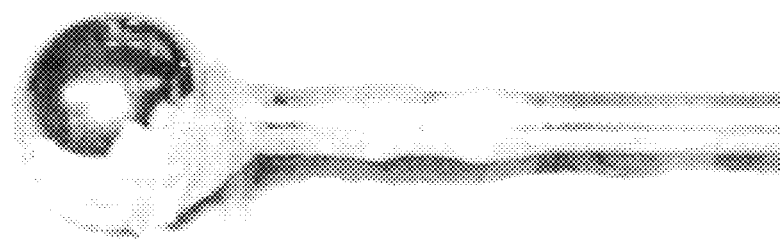
FIGS. 1A and 1B show images of coated substrates.

The present invention accordingly describes antimicrobial coatings comprising a hydrogel layer and a bioactive agent comprising at least one substantially water-insoluble antimicrobial metallic material that is homogeneously dispersed and maintained in a substantially "solubilized" form within the coating.

The term "solubilize" with reference to the substantially water-insoluble antimicrobial metallic material in the antimicrobial coatings of the invention as used herein, refers to a homogeneous or substantially homogenously dispersed composition of the substantially water-insoluble antimicrobial metallic material within in the coating hydrogel layer. The term "solubilized" with reference to the substantially water-insoluble antimicrobial metallic material in the antimicrobial coating formulations of the invention as used herein, refers to a homogeneous or substantially homogenous dispersion of the substantially water-insoluble antimicrobial metallic material in the coating formulation or coating solution of the invention containing the hydrophilic polymers used to obtain the antimicrobial coatings of the invention. The term "solubilization" with reference to the substantially water-insoluble antimicrobial metallic material in the antimicrobial coatings and antimicrobial coating formulations of the invention as used herein, refers to the dissolution of the substantially water-insoluble antimicrobial metallic material in the coating material or coating formulation in a homogeneous or substantially homogenous manner.

By maintaining the water-insoluble antimicrobial metallic material in a homogeneously dispersed solubilized form, high concentrations of the water-insoluble antimicrobial metallic material may be incorporated in relatively thin coatings, which is not achievable in heterogeneous compositions incorporating it in a micronized form. The antimicrobial coatings of the invention, therefore, provide high concentrations of the antimicrobial metallic material in a contacting aqueous environment over extended periods of time, and effectively inhibit bacterial adhesion and biofilm formation on the coating surface. For example, The "solubilization" of AgSD in the antimicrobial coating of the invention enables thin coatings comprising high (therapeutic) levels of AgSD that is up to two orders of magnitude higher with respect to its soluble levels in water. Such levels in thin coatings are unachievable with micronized AgSD, thereby precluding their application to small dimension medical devices, for which a thin coating (coating thickness dimension of several micrometers ($\mu$M) is an essential prerequisite. Such devices include, but are not limited to catheters, stents, wound drains, needle-less connectors, trauma pins etc., that have diameters of only a few millimeters.

Although the invention as claimed is not to be construed as relying upon any hypothesis as to the mode of action, it can be reasonably inferred that the homogeneous dispersion of the water-insoluble silver compounds in a "solubilized" form within the hydrogel coating whereby they are substantially homogeneously dispersed within the coating, enables incorporation high concentrations of such silver compounds in relatively thin coatings per unit area of coating, which in turn, results in bactericidal $Ag^+$ ions to be released from the hydrogel coating into the contacting aqueous environments. Furthermore, the relatively small coating thickness coupled with the hydrophilic nature of the polymeric material forming the cross-linked hydrogel coating matrix enable the facile diffusion of $Ag^+$ ions from the solubilized silver compounds homogenously dispersed within the coating, that results in extended duration of coating antimicrobial efficacy. The cross-link density in the 3-D hydrogel matrix forming the coating may be varied to effectively control the diffusion rate of $Ag^+$ ions released from the coating, thereby providing control over the duration of coating antimicrobial efficacy. The substantially water-insoluble silver compounds that are rendered soluble in the hydrophilic coating formulations of the invention enable high concentrations of the insoluble silver compounds that are homogeneously dispersed within the coating to be incorporated into relatively thin coatings, thereby enabling controlled release of higher concentration of Ag+ ions per unit area of the coating, compared to relatively thicker coatings that are required when the water insoluble silver compounds are present in a heterogeneous micro-particular phase.

The hydrogel layer in the antimicrobial coating of the present invention comprises a three-dimensional network formed by a hydrophilic polymer by ionic or chemical cross-linking, cryogel formation, or by an interpenetrating polymeric network. The hydrophilic polymer of the invention is chosen from polyfunctional water soluble polymers, including polyfunctional polymers such as, for example, polyvinyl alcohol, polyvinylpyrrolidone, polyethyleneimine, polyacrylic acid, polyhydroxyethylmethacrylate, polylactic acid, polylactide, polyglycolide, poly epsilon-caprolactone, copolymers and mixtures thereof, poly vinyl alcohol-glycine co-polymer, and polyvinyl alcohol-lysine co-polymer. Ionic or chemical crosslinking of the hydrophilic polymers can be accomplished in the polyfunctional polymers included in the antimicrobial coatings of the invention. For example, a hydrogel layer comprising ionically cross-linked hydrophilic polymer chains by coating a substrate material with the antimicrobial coating formulation of the invention comprising a polyfunctional hydrophilic polymer containing coating formulation and a substantially water-insoluble antimicrobial metallic material in a solubilized homogeneous dispersion on a substrate surface, drying the coating to a pre-determined extent and reacting it with a suitable ionic or chemical crosslinking agent or agents known in the art. The cross-linking agent is chosen appropriately based on its ability to effect cross-linking between functional groups present in the polyfunctional hydrophilic polymer chains. Examples of ionic cross-linking agents include, but are not limited to, divalent or trivalent metal halides such as calcium, zinc or copper halides. Examples of covalent cross-linking agents include, but are not limited to aldehydes, dialdehydes, alkyl dihalides, alkyl ditriflates, etc.

In one embodiment, chemical cross-linking is accomplished in partially or completely dried coatings on a substrate surface utilizing the antimicrobial coating formulations of the invention that comprise a hydrophilic polymer and a solubilized substantially water-insoluble antimicrobial metallic material, drying the coating for an appropriate amount of time and reacting it with a chemical crosslinking agent capable of reacting with the functional groups in the hydrophilic polymer chains. Cross-link density in the hydrogel matrix forming the antimicrobial coatings of the invention may be controlled or pre-determined by varying the concentration of the cross-linking reaction, by appropriately varying the reaction time of the cross-linking process, by varying the time between coating and cross-linking, and/or reaction temperature of the cross-linking reaction.

In a currently preferred embodiment, the hydrophilic polymer in the coating formulation of the invention is poly(vinyl alcohol) (PVA). Poly(vinyl alcohol), which is commercially available in several forms that differ in percent hydrolysis and molecular weight range. The antimicrobial coatings of the present invention utilizes an optimal combination of these characteristics of PVA, together with control of cross-link density to pre-determine coating physical properties, including tensile strength, durability and pore size. In one preferred embodiment, the PVA in the antimicrobial coating formulations of the invention has a percent hydrolysis ranging between 87 to 89%. In another preferred embodiment, the PVA in the antimicrobial coating of the invention includes a form with percent hydrolysis of greater than about 99%. The molecular weight of PVA used in the antimicrobial coating formulations of the invention ranges between 124,000 to 186,000 daltons. In another embodiment, the molecular weight of PVA ranges from 89,000 to 98,000 daltons. In a currently preferred embodiment, the choice of PVA includes, but is not limited to a hydrolysis percent that are about 87-89% and a molecular range between 124,000 to 186,000 daltons, 99+% hydrolysis, molecular weight range 124,000 to 186,000; a hydrolysis percent that is ≥99% and a molecular weight range between 89,000 to 98,000, and combinations thereof. The PVA in the antimicrobial coatings of the invention may comprise a single hydrolyzed form (in terms of % hydrolysis) and molecular weight range, or may comprise a mixture of two or more PVA types (% hydrolysis and molecular weight ranges). The concentration of PVA in the antimicrobial coating formulations of the invention typically ranges between 0.1 and 1000 g/L. In a currently preferred embodiment, the concentration of PVA having 87-89% hydrolysis, and a molecular weight range of 124,000 to 186,000 is 50 g/L.

The cross-linking agents for the PVA based antimicrobial coatings of the present invention include a mono- or dialdehyde monomer or a diol. Examples of aldehyde cross-linking agents include, but are not limited to, formaldehyde, paraformaldehyde, glyoxal, or glutaraldehyde. The cross-linking agent may be added to the hydrophilic polymer in the form of a solution. In one embodiment, the cross-linking solution is maintained at an acidic pH. In a currently preferred embodiment, the cross-linking agent comprises 3% formaldehyde and 1% glyoxal in a solution of 1% hydrochloric acid. In another embodiment, chemical cross-linking is accomplished in partially or completely dried coatings on a substrate surface obtained from the antimicrobial coating formulations of the invention comprising PVA and a solubilized substantially water-insoluble antimicrobial metallic material on a substrate, drying the coating for an appropriate amount of time and reacting it in a chemical cross-linking step using a suitable aldehyde by contacting the PVA coating to a solution containing the aldehyde cross-linking agent. Cross-link density in the hydrogel matrix forming the antimicrobial coatings of the invention may be controlled or pre-determined by varying the concentration of the cross-linking reaction, by appropriately varying the reaction time of the cross-linking process, by varying the time between application of the coating and cross-linking agents, and/or reaction temperature of the cross-linking reaction. In a currently preferred embodiment, the cross-linking agent comprises a solution containing 3% formaldehyde and 1% glyoxal in a solution of 1% Hydrochloric acid.

The bioactive agent in the antimicrobial coatings of the invention comprises a substantially water-insoluble antimicrobial water-insoluble material including an antimicrobial metal, metal alloy, metal salt, metal or metal complex that is maintained in a solubilized form in the hydrogel layer of the antimicrobial coating, and optionally, combined with a non-metallic antimicrobial or antibiotic compound. Such substantially water-insoluble antimicrobial metallic materials include, but are not limited to antimicrobial metal salts and metal complexes of silver, copper and zinc. In a preferred embodiment, the substantially water-insoluble antimicrobial metallic material is a substantially water insoluble antimicrobial silver compounds including, but not limited to, silver halides, silver sulfazines, silver sulfadiazines, silver sulfonamides and silver sulfonylureas. In a currently preferred embodiment the substantially water-insoluble antimicrobial metallic compound is silver sufladiazine, (AgSD).

Figure 1B:

In a preferred embodiment, the antimicrobial coating formulations of the invention comprises AgSD in a range from about 1 mg/L to about 100 g/L. In a currently preferred embodiment, the concentration of AgSD is about 20 g/L. In a second preferred embodiment the concentration is 30 g/L. These concentrations of AgSD in the coating formulations of the invention enable the formation of relatively thin coatings that comprise high AgSD loading and reservoir capacity that provides bactericidal levels of $Ag^+$ ions and sulfadiazine into the contacting environment. For example, a 15 μm thick coating obtained from a antimicrobial coating formulation having an AgSD concentration of 20 g/L, provides approximately 70 μg/cm$^2$ of solubilized AgSD in the resulting coating that provides bactericidal levels of $Ag^+$ ions and sulfadiazine into the contacting environment. The antimicrobial coatings of the invention which provide high concentrations of AgSD per unit area of coating for very thin coatings (<100 μM) due to the solubilization of AgSD within the coating, therefore overcome a major limiting factor that exist in the conventional method of utilizing of micronized AgSD. Based on the substantially low solubility of AgSD in aqueous solutions (~6×10$^{-4}$ moles/L AgSD equivalent to ~0.22 grams/L AgSD) a coating containing micronized AgSD would have to be about 2.5 mm thick in order to produce a similar loading of about 70 μg/cm$^2$. Coatings containing micronized AgSD in the absence of other water-soluble antibacterial agents are therefore, not only impractical for coating medical devices with small dimensions, but also result in coatings that have defects and poor mechanical properties. The advantages of the coatings of the present invention comprising solubilized AgSD and the deficiencies of a similar coating on a stainless steel piercing containing micronized AgSD are shown in FIG. 1B. As seen in FIG. 1A, a hydrophilic PVA coating containing micronized AgSD is relatively thick, opaque and has considerable defects in terms of both coating uniformity and coating integrity, whereas the PVA coating of the present invention comprising solubilized AgSD shown in FIG. 1B is highly uniform, thin and transparent with good coating integrity.

The antimicrobial coatings and coating formulations of the invention additionally comprises a stabilizing compound that maintains the substantially water-insoluble antimicrobial metallic material in a solubilized form within the coating hydrogel layer. The presence of a stabilizing compound, for example an antioxidant such as $TiO_2$, imparts a protective effect to the antimicrobial coatings of the invention against discoloration of the coating during exposure to light, thereby rendering the coatings to be photostable.

Without wishing to be bound by theory, it is believed that the presence of a stabilizing compound in the antimicrobial coatings of the invention, such as an antioxidant, photostabilizer or free-radical scavenger in the coating is believed to impart a protective effect that prevents the reduction of AgSD and the diffusing $Ag^+$ ions from ionized AgSD diffusing from within the coating to particulate metallic silver)($Ag^0$) that is antimicrobially inert, thereby maintaining the AgSD in an antibacterially active solubilized form that provides bactericidal amounts of $Ag^+$ ions into the contacting environment.

In one embodiment, the antimicrobial coating composition additionally comprises a stabilizer compound such as an antioxidant, photostabilizer or free-radical scavenger compound or mixtures thereof. Any suitable antioxidant may be used. Antioxidants include, but are not limited to, lactones, phenolics, phosphites, thioesters, hindered phenolics such as, for example, 1,3,5-tris(4-tert-butyl-3-hydroxy-2,6-dimethylbenzyl)-1,3,5-triazine-2,4,6-(1H,3H,5H)-trione (Cyanox®1790), hindered amines such as, for example, poly[(6-morpholino-s-triazine-2,4-diyl)[2,2,6,6-tetramethyl-4-piperidyl)imino]-hexamethylene[(2,2,6,6-tetramethyl-4-piperidyl)imino]] (Cyasorb®UV-3346), and hindered benozoates such as, for example, 3,5-di-t-butyl-4-hydroxybenzoic acid, hexadecyl ester (Cyasorb®UV-2908). Cyanox®1790, Cyasorb®UV-3346 and Cyasorb®UV-2908 are distributed by Cytec Industries Inc., West Paterson, N.J. Vitamin E (alpha-tocopherol), TPGS (alpha-tocopherol polyetheylene glycol succinate), BHT (alpha-lipoic acid, butylated hydroxy toluene) and ascorbate (sodium ascorbate) may also be suitable antioxidants, particularly in a water soluble form. Photostabilizing compounds include, but are not limited to, benzoates, benzophenone, benzotriazole, cyanoacrylate, organo nickel and organo zinc and compounds such as magnesium silicate. Stabilizers include, but are not limited to titanium dioxide ($TiO_2$) and tungsten trioxide ($WO_3$) in any of their polymorphic forms. In one embodiment, the antioxidant is $TiO_2$.

In a preferred embodiment, the concentration of titanium dioxide ($TiO_2$) in the antimicrobial coating formulation ranges from ranges between 0.1 g/L and 10.0 g/L. In a currently preferred embodiment, the concentration of $TiO_2$ is about 2 g/L. The $TiO_2$ is preferably micronized by standard methods, such as for example, using a jet milling process, to have an average particle size ranging between 0.1 to 20 μm. In a currently preferred embodiment, the average particle size of the micronized $TiO_2$ is about 1 μm. In another currently preferred embodiment, a commercial grade, submicron particulate $TiO_2$ with an average particle diameter of <45 nanometers (nm) is used as an antioxidant stabilizer compound in the antimicrobial coating formulations of the invention.

The presence of a stabilizer compound in the antimicrobial coatings of the present invention maintain the AgSD in a solubilized form and inhibit the reduction of AgSD and the $Ag^+$ ions generated from the AgSD (including photoreduction) to metallic silver that is antimicrobially inactive, and therefore, maintains high coating antimicrobial efficacy, and provides relatively faster, and longer kill rates in comparison to coatings without a stabilizer compound. The presence of $TiO_2$ as a stabilizer compound in the antimicrobial coatings of the invention containing solubilized AgSD, for example, results in improved antimicrobial efficacy demonstrated by faster kill rates relative to coatings containing solubilized AgSD alone.

The effect of a stabilizer compound on the activity of solubilized AgSD was confirmed by an in-vitro antimicrobial assay in aqueous solutions containing 0.5 μg/mL of dissolved AgSD (to simulate solubilized AgSD in the coatings of the invention) with and without added $TiO_2$ (0.3 μg/mL) that were challenged with ~$10^4$ cfu/mL of *staph. epidermidis* for 60 minutes. The test results (summarized in Table 1 below) show that AgSD solution containing $TiO_2$ exhibits faster kill rates in 60 minutes (100%) compared to the AgSD solution without $TiO_2$ (40%) relative to control, while a $TiO_2$ containing solution without AgSD is not antibacterial, thereby substantiating the stabilizing influence of $TiO_2$ in maintaining the AgSD in a soluble form and preventing the reduction to metallic silver.

TABLE 1

Effect of stabilizer compound (TiO2) on the antimicrobial efficacy of PVA-solubilized AgSD coating at t = 60 minutes.

| % Reduction Control | % Reduction AgSD | % Reduction AgSD + $TiO_2$ | % Reduction $TiO_2$ |
|---|---|---|---|
| 0 | ~40 | 100 | 0 |

In yet another embodiment, the bioactive agent in the antimicrobial coatings of the invention comprises one or more antibacterial or antibiotic agents in addition to the solubilized, substantially water-insoluble metallic material. These include antibiotics such as but not limited to rifampin, gentamicin, vancomycin, neomycin, soframycin, bacitracin, polymycin, synthetic antibiotics including ofloxacin, levofloxacin and ciprofloxacin, antibacterials including biguanides such as chlorhexidine and their salts, alkyl ammonium halides such as benzalkonium chloride cetrimide, domiphen bromide and phenolics such as triclosan.

The antimicrobial coating formulation of the present invention comprise coating solutions that include at least one hydrophilic polymer that is dissolved in an appropriate solvent, and a bioactive agent comprising a substantially water-insoluble antimicrobial metallic material that is solubilized in the coating solution so as to form a homogeneous phase or a substantially homogeneous phase with the hydrophilic polymer. The coating solutions of the invention comprise one or more water-soluble hydrophilic polymers having polyfunctional groups, including but not limited to polyvinyl alcohol, polyvinylpyrrolidone, polyethyleneimine, polyacrylic acid, polyhydroxyethylmethacrylate, and copolymers and mixtures thereof. In a currently preferred embodiment, the coating solutions of the invention comprise an aqueous solution of polyvinyl alcohol (PVA). The substantially water-insoluble antimicrobial metallic material is chosen from, but not limited to, antimicrobial metal salts and metal complexes of silver, copper and zinc. In a preferred embodiment, the substantially water-insoluble antimicrobial metallic material is a substantially water insoluble antimicrobial silver compounds including, but not limited to, silver halides, silver sulfazines, silver sulfadiazines, silver sulfonamides and silver sulfonylureas. In a currently preferred embodiment the substantially water-insoluble antimicrobial metallic compound is silver sufladiazine, (AgSD).

In another preferred embodiment, antimicrobial coating formulations of the present invention additionally comprise a stabilizer compound that maintains the substantially water-insoluble antimicrobial metallic material, which is solubilized in the coating formulation, in a solubilized form in coatings obtained from the coating formulations. Examples of such stabilizer compounds include antioxidant, photostabilizer or free-radical scavenger compounds, or mixtures thereof. Stabilizer compounds include, but are not limited to $TiO_2$ and $WO_3$ in any of their polymorphic forms. Photostabilizing compounds include compounds such as magnesium silicate. In a currently preferred embodiment, the stabilizer compound is $TiO_2$.

The substantially water-insoluble antimicrobial metallic material is dissolved in an aqueous acidic solution at an elevated temperature so as to effect complete dissolution of the metallic material. The acidic solution containing the dissolved antimicrobial metallic material is then mixed with an aqueous solution of the hydrophilic polymer so as to maintain the antimicrobial metallic material in a solubilized form in the solution mixture in a homogeneous or substantially homogeneous aqueous phase, wherein the antimicrobial metallic material and the hydrophilic polymer are homogeneously dispersed in the aqueous coating solution.

In a currently preferred embodiment, a pre-determined amount of silver sulfadiazine is added to an aqueous solution of heated dilute nitric acid to bring the desired concentration of AgSD into solution. The heated AgSD/nitric acid solution is stirred and heated between about 65° to about 70° C. Following the complete dissolution of the AgSD, a pre-determined amount of PVA having the desired percent hydrolysis and molecular weight range is added with stifling. The PVA/AgSD/nitric acid solution is stirred and heated until all components are dissolved. The viscosity of the resulting coating solution comprising the PVA and solubilized AgSD ranges from about 10 to about 30 centipoises (cP), depending on the characteristics of the PVA used. In a particularly preferred embodiment, the viscosity of the coating formulation is about 20 cP, the nitric acid concentration is about 1 Molar, and the temperature of dissolution is about 70° C. In another embodiment, the AgSD solution in aqueous nitric acid is further mixed with buffer solution, such as for example, a phosphate buffer, prior to addition of PVA.

In another preferred embodiment of the invention, the coating formulation of the invention comprises a coating solution containing a hydrophilic polymer dissolved therein, a bioactive agent comprising a antimicrobial metallic material that is solubilized in the coating solution, and at least one stabilizer compound that is either dissolved in the coating solution to form a homogeneous phase, or suspended in the coating solution as a microparticulate dispersion. In a currently preferred embodiment, the stabilizer compound is an inorganic oxide antioxidant compound, namely $TiO_2$, which is suspended as a microparticular dispersion in the coating formulation. In a currently preferred embodiment, micronized $TiO_2$ is mixed with dry PVA to obtain a dry powder mixture that is added to a stirred solution of aqueous acidic AgSD solution while maintaining an elevated temperature, preferably between 75° and 80° C. to obtain a coating formulation suspension containing PVA, solubilized AgSD in which the $TiO_2$ is evenly dispersed. The resulting coating solution containing PVA, solubilized AgSD and the $TiO_2$ suspension is mixed additionally for 1 to 5 hours. Alternatively, the $TiO_2$ is added to an aqueous solution of PVA to obtain a suspension, and PVA/$TiO_2$ suspension is then added to a stirred aqueous acidic AgSD solution while maintaining an elevated temperature, preferably between 75° and 80° C.

The coating formulations of the invention is applied on a substrate surface using any of the standard coating methods known in the art such as dipping, spraying, rolling, etc. In a preferred embodiment, the coating formulations are applied on substrate materials using a dipping process. In a one embodiment, the substrate is dipped into the coating material at a temperature ranging from 35 about to about 41° C., preferably at 38° C., for about 1 to 60 seconds. The substrate is then mechanically withdrawn from the coating material such that a uniform coat is achieved. The antimicrobial coatings of the invention comprising a bioactive agent that includes a solubilized antimicrobial metallic material and optionally, a stabilizer compound of are obtained by applying the antimicrobial coating formulations of the invention on a substrate material, subjecting the coating to either a partial or complete drying step, followed by reacting the coatings formed thereby to a cross-linking step. The coatings of the invention may be produced on substrate materials either in their unfinished form (sheet, granules, pellets etc.) or a finished product such as a medical device or healthcare product. When the substrate to be coated contains a lumen, a vacuum or positive pressure may be applied to during the coating process to ensure that all parts of the substrate are contacted with the coating formulation. The substrate material is optionally subjected to a spin step to aid in vertical and radial consistency of the resulting coating when utilizing a dip process during the withdrawal of the substrate material from the coating formulation. In one embodiment the spin rate during coated substrate material withdrawal is maintained between 0-25 rpm. In one embodiment, the withdrawal speed ranges between about 0.25 to about 10 mm/sec, and preferably, about 5.0 mm/sec.

In another embodiment, the antimicrobial coating formulations of the invention comprising coating solutions are applied to the surface of a substrate material by a spray coat method. The antimicrobial coating formulations is sprayed on the substrate material surface using standard spraying equipment and methods known in the art. Suitable spraying equipment include, but are not limited to, sprayers using pressurized air, and sprayers using an ultrasonic spray head, both of which aerosolize the coating solutions. PVA molecular weight range, weight percentage, and percent hydrolysis are appropriately chosen so as to maximally aerosolize the coating solution. In a currently preferred embodiment, a PVA with molecular weight range of 89,000 to 98,000 and 99+% hydrolysis is combined with PVA with a molecular weight range of 31,000 to 50,000 and 87-89% hydrolysis in a ratio of 2:5 or 100 and 250 g/L respectively.

In another embodiment, the antimicrobial coating of the present invention comprises a plurality of individual coating layers or "coats" that is obtained by a series of coating formulation application and drying steps performed simultaneously and optionally, including an additional cross-linking step after one or more drying steps, thereby enabling the control of elution kinetics as well as the concentration of the antibacterial/antimicrobial compound. For example, by overlaying two coating layers of approximately the same thickness, the effective concentration of AgSD released per $cm^2$ of the coated substrate is effectively doubled. Other variations include excluding the cross-linking step in the inner layers of with a multiple-layer coating, and limiting the cross-linking to the outermost coating layer.

The coating layer formed on substrate material surface by any of the methods described hereinabove is then dried by a suitable drying process that include, but not limited to, air-drying, infrared radiation, convection or radiation drying (e.g. a drying oven), or warm forced air (e.g. heat gun). The drying step is performed both before and after contacting the coating with a cross-linking agent. In the case of multi-layer coatings, the drying step may be performed after formation of each of the inner layers without contacting a cross-linking agent, while it is performed on the outermost layer after contacting the cross-linking agent. The drying time and drying temperature alter the elution kinetics of the antimicrobial coatings of the invention. Longer drying times at a given temperature produces less cross-linking and therefore, result in relatively faster drug release profiles. Typically, drying of the coated substrate materials is accomplished by means of a "heating iris" or plenum, which the substrate is withdrawn through, that is located proximally (approximately two inches) from the surface of the coating formulation which the substrate material or finished product is being dipped, or alternatively, from the surface of the coated substrate material of finished product when the coating is applied by a spray method. Heating of the coated substrate material is accomplished for example, with a hot air blower that provides a temperature of about 60° to about 70° C. and airflow of several liters per minute to the plenum. Such an airflow is usually directed circumferentially around the part during withdrawal and spin process of the substrate material from the coating formulations. Cross-linking of the coating layer to obtain the hydrogel network in the antimicrobial coatings of the invention is accomplished by contacting a partially or completely dry coating layer on the substrate material with a cross-linking agent by immersion of the coated substrate material or finished product into a solution comprising the cross-linking agent either prior to after the drying step following which the coating is subjected to additional drying at elevated temperature for a pre-determined time to induce cross-linking. Alternatively, the cross-linking agent may also be applied to the substrate by spray coating the substrate first with coating material, and secondly with a solution containing the cross-linking agent(s). In a currently preferred embodiment the cross-linking solution contains 1% glyoxal, 3% formaldehyde, and 1% HCl.

The coating formulations of the invention may be applied to a variety of substrate materials, including but not limited to synthetic and naturally occurring organic and inorganic polymers such as polyethylene, polypropylene, polyacrylates, polycarbonate, polyamides, polyurethane, polyvinylchloride (PVC), polyetherketone (PEEK), polytetrafluroethylene (PTFE), cellulose, silicone and rubber (polyisoprene), plastics, metals, glass, and ceramics. While the coating formulations of the invention may applied either directly on materials with a hydrophilic surface such as metals, glass and cellulose or optionally on top of a primer undercoat, materials with hydrophobic surfaces such as silicone and PTFE are subject to a surface pre-treatment step prior to application of the coating.

Substrates that are not wettable by the coating formulations of the invention, particularly hydrophobic substrates such as silicone, polytetrafluoroethylene (PTFE) etc., are surface pre-treated prior to coating. The surface pre-treatment process involves either coating the hydrophobic substrate with a primer layer on which the antimicrobial coatings of the invention are deposited, or a surface modification step wherein the surface of the substrate material is subjected to an oxidation process that is optionally followed by a chemical grafting reaction to render the surface hydrophilic, and compatible with the coating formulations of the invention. In one embodiment, the surface pre-treatment of the substrate material involves a plasma oxidation process under reduced pressure, followed by chemical grafting of an aliphatic alcohol. In a currently preferred embodiment, the aliphatic alcohol is allyl alcohol. The power settings, gas flow rates, times, and pressures are maintained optimally during the surface oxidation process, and during grafting of alcohol The coating thickness of the antimicrobial coatings of the invention are controllable by optimal choice of substrate withdrawal speed from the coating formulations after immersion, coating solution viscosity, coating solution temperature, number of coats applied, and substrate material spin speed. The coating thickness can be pre-determined by controlling the temperature of the PVA/AgSD during the dip process, the viscosity of the coating formulation during immersion of the substrate material or finished product, e.g. a medical device or healthcare product, withdrawal speed and technique (spinning, etc.), coating method (e.g. spray instead of dip), number of dip/spray cycles and immersion/spray time. In one embodiment, a coating with thickness of about 10-20 μm is obtained by maintaining the withdrawal speed at 5 mm/sec, the coating viscosity at 20 cP, and the coating solution temperature at 38° C. and substrate material spin rate at 5 rpm. In another preferred embodiment, the withdrawal speed of the substrate is varied as the part is withdrawn to account for the time variation of immersion time from the bottom to the top of the length of the substrate. The withdrawal speed (rate of withdrawal) the substrate material or finished product from the coating formulation is either maintained at a constant value, or is varied during the withdrawal process. In a currently preferred embodiment, the withdrawal speed is maintained initially at 5 mm/sec, and subsequently changed to 6 mm/sec after about ⅓ of the of the substrate material or finished product (e.g. length if the product has a linear configuration, such as for example, a catheter) has been withdrawn from the coating formulation, and further changed to 7 mm/sec after withdrawal of ⅔ of the substrate material or finished product. The coating thickness of the antimicrobial coatings of the invention can be used to effectively control the amount and duration of bioactive agent release in a contacting environment. The coating thickness of the antimicrobial coatings of the invention ranges between 5 μm to 100 μm, while bioactive agent loading in dry coatings range between 10 to 300 μm/cm² of coated surface area.

Figure 2A:
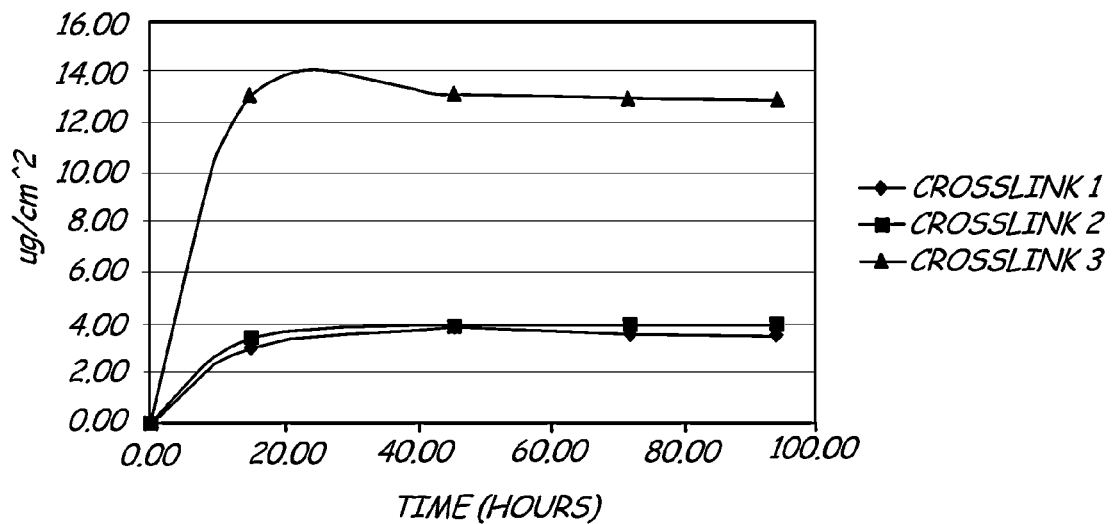
FIGS. 2A and 2B show coating AgSD elution profiles of static and dynamic elution assays.
Figure 2B:
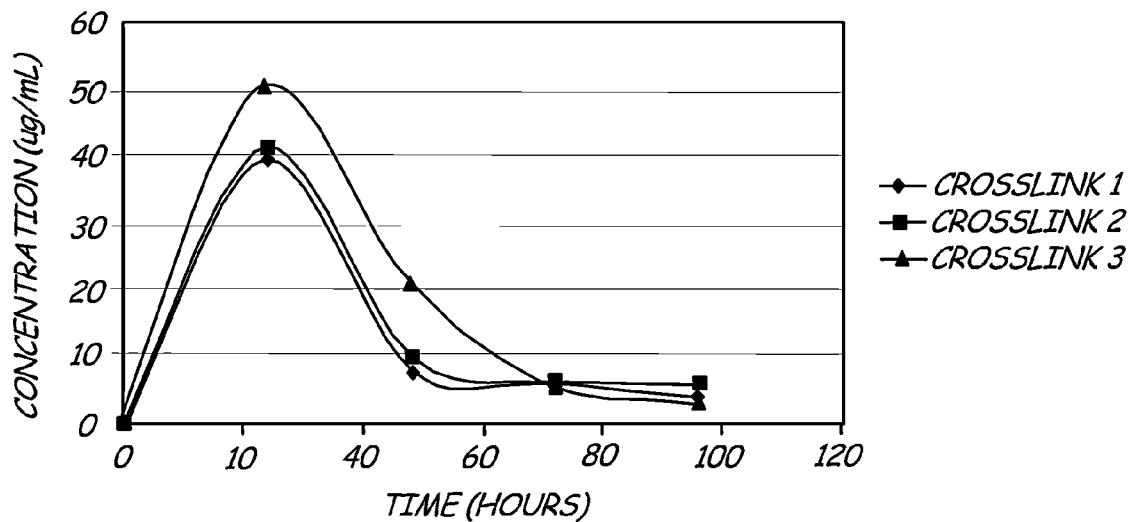
Figure 3:
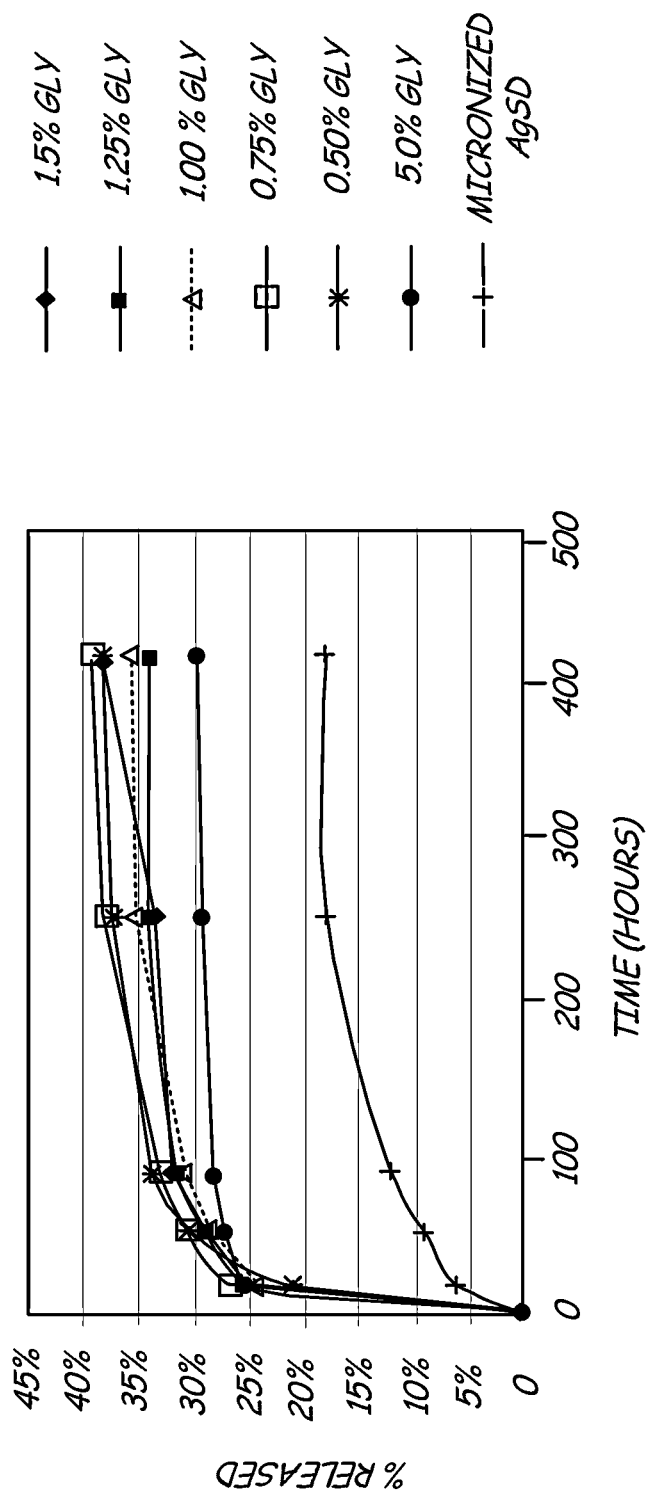
FIG. 3 shows coating AgSD elution profiles as a function of crosslink density.

Release of bioactive agent, in particular, the solubilized antimicrobial metallic material is measured in an elution assay. Both static and dynamic elution assay methods described herein may be used to estimate the released bioactive agent. Typical static and dynamic elution profiles for AgSD as a function of coating cross-link density in the antimicrobial coatings of the invention are shown in FIGS. 2A and 2B, respectively, which measure the total AgSD released from the coating. As seen in FIG. 3, the elution profiles for AgSD antimicrobial coatings of the invention indicate that higher concentrations of sulfadiazine (SD) and correspondingly a higher level of $Ag^+$ ions are released into the contacting aqueous environment at a fairly constant rate at lower coating cross-link densities (e.g. 1.5% glyoxal), and a substantially constant rate at relatively higher cross-link densities (e.g. 5% glyoxal) over a period of over 400 hours. In contrast, a previously known hydrophobic coating micronized AgSD provides substantially lower levels of SD and $Ag^+$ ions under similar conditions (FIG. 3). The hydrophilic antimicrobial coatings of the present invention therefore, offer the advantage of conferring coated surfaces with higher antimicrobial efficacy towards inhibition of bacterial adhesion and biofilm formation on coated substrate materials and finished products such as medical devices and healthcare products over a long duration of time, compared with hydrophobic coatings containing micronized AgSD.

Figure 4A:
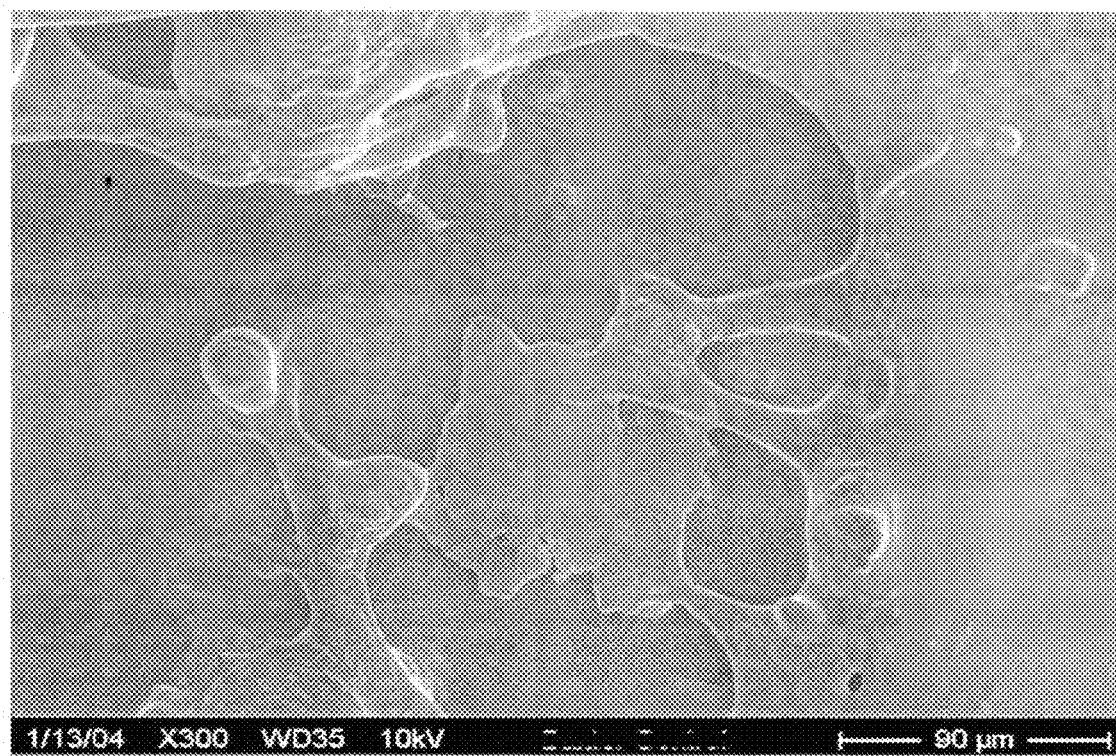
FIGS. 4A and 4B show Scanning Electron Microscope (SEM) images of coated and uncoated substrates.
Figure 4B:
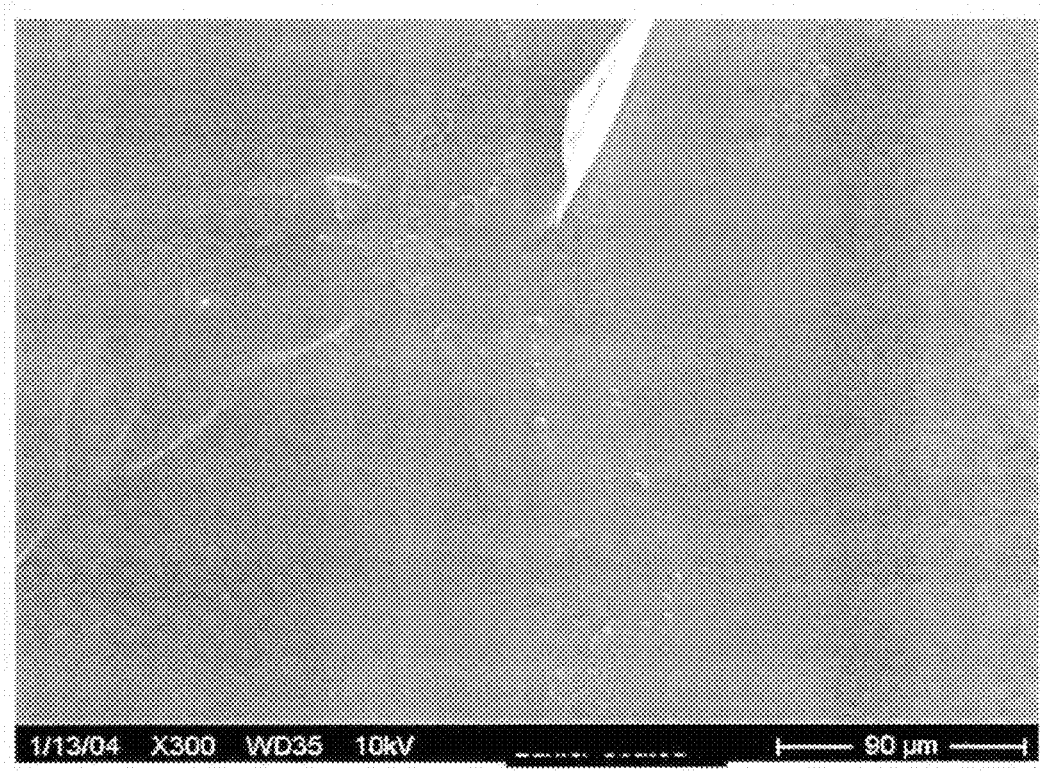

The antimicrobial coatings of the present invention are effective in preventing bacterial adhesion and subsequent biofilm formation on coated surfaces. FIGS. 4A and 4B show scanning electron micrographs of coated and uncoated outlet housing components of a medical device that were maintained in contact with *S. epidermidis*, which is a bacteria that is responsible for colonizing the surface of implanted medical device such as catheters that results in biofilm formation. The uncoated housing (control) shows well developed biofilm formation resulting from bacterial adhesion and proliferation on the component surface (FIG. 4A), while the housing component coated with the antimicrobial coating of the present invention shows virtually no bacterial adhesion or biofilm formation (FIG. 4B).

Further, the antimicrobial coatings of the invention are also stable in physiologic environments such as urine, blood, plasma, and are stable to commonly used terminal stabilization methods for medical devices. The antimicrobial coatings of the present invention can be obtained on a variety of substrate materials, including those commonly used in the manufacture of medical devices and healthcare products and on the finished products themselves. Examples of medical devices or healthcare products that are coated with the antimicrobial coatings and coating formulations of the invention to obtain antimicrobial coatings that inhibit bacterial adhesion and biofilm formation include, but are not limited to, a urological catheters, central venous catheters, wound drains, orthopedic implants, dental implants, feeding tubes, tracheal tubes, and medication delivery products (e.g. needle-less connectors and/or IV products).

The methods of manufacturing the coatings and coating compositions of the invention and their analysis are described in the following examples which are not intended to be limiting in any way.

EXAMPLES

Example 1

Coating Formulation Containing Solubilized Silver Sulfadiazine (AgSD)

A coating formulation comprising AgSD (20 g/L) was prepared as follows. Nitric acid (64 mL, 70%) was added to 800 mL $H_2O$. The resulting nitric acid solution was then heated to 70° C. using a double boiler. AgSD (20 g) was added to the nitric acid solution with stirring using and overhead stirrer with a dissolving stifling shaft. The AgSD was dissolved in a couple minutes. The final volume of the AgSD solution was brought to 1.0 L with $H_2O$.

Additional coating ingredients may be added when the AgSD (20 g/L) coating formulation is complete. Higher concentrations of AgSD such as 30 g/L may be prepared using analogous procedures.

Example 2

Coating Formulation Preparation

A liter of coating formulation comprising AgSD (20.0 g) and PVA (50.0 g, MW=124,000 to 186,000, 87-89% hydrolysis) was prepared as follows.

In an appropriate sized temperature controlled mixing vessel set at moderate mixing, Nitric acid (64 mL, 70%) was added to purified $H_2O$ and diluted to 800 mL. The temperature of the circulating heater with oil & pump was set between 65° C. and 70° C. The variable speed overhead mixer with dissolving stirrer attachment was set at 500 rpm. AgSD 20.0 g was added slowly to the mixing water and acid mixture. The solution was mixed for a minimum of 15 minutes. The dissolution was confirmed by turning off the mixer and observing that no solid particles settle out after 60 seconds. The temperature of the circulating heater was set to 80° C. and the stirrer was turned back on. The temperature in temperature controlled vessel containing the drug/acid mixture was allowed to reach at least 75° C. before proceeding.

While maintaining the temperature between 75° C. and 80° C., 50.0 g of polyvinylalcohol was added to the acid/water AgSD solution with stifling at 500 rpm. The solution was mixed for an additional 3 hours at 500 rpm. The resulting PVA coating formulation was a light yellow color and had a smooth appearance in about an hour after the last component was added. The final volume of coating was brought up to 1.0 L with purified water.

The PVA coating formulation may be stored at room temperate in a covered/sealed container until it is used. The PVA coating formulations are stable for about 5 days after preparation at ambient temperature, and about 3 months at about 38° C. The PVA coating formulation may normally be used at 38° C. Alternatively, the PVA coating formulation may stored at room temperature, and heated to its application temperature, with mixing, for about 24 hours prior to use ensuring that all components are in solution and well mixed. The PVA coating formulation may be additionally screened through the 20×20 stainless steel screen before being stored or used in the coating processes.

Example 3

Coating Formulation Preparation with $TiO_2$

A liter of coating formulation comprising AgSD (20.0 g), PVA (50.0 g, MW=124,000 to 186,000, 87-89% hydrolysis) and $TiO_2$ (2.0 g) was prepared as follows.

In an appropriate sized temperature controlled mixing vessel set at moderate mixing, Nitric acid (64 mL, 70%) was added to purified $H_2O$ and diluted to 800 mL. The temperature of the circulating heater with oil & pump was set between 65° C. and 70° C. The variable speed overhead mixer with dissolving stirrer attachment was set at 500 rpm. AgSD 20.0 g was added slowly to the mixing water and acid mixture. The solution was mixed for a minimum of 15 minutes. The dissolution was confirmed by turning off the mixer and observing that no solid particles settle out after 60 seconds. The temperature of the circulating heater was set to 80° C. and the stirrer was turned back on. The temperature in temperature controlled vessel containing the drug/acid mixture was allowed to reach at least 75° C. before proceeding.

Micronized Titanium dioxide (2.0 g) was added to 50.0 g of dry PVA powder. The two powders are well mixed with each other, before being added together to the AgSD solution. While maintaining the temperature between 75° C. and 80° C., the PVA Titanium Dioxide mixture was added to the acid/water AgSD solution with stirring at 500 rpm. The solution was mixed for an additional 3 hours at 500 rpm. The resulting PVA coating formulation was a light yellow color and had a smooth appearance in about an hour after the last component was added. The final volume was brought to 1.0 L with purified water.

The PVA coating formulation may be stored at room temperate in a covered/sealed container until use. The PVA coating formulation may have a shelf life of about 5 days from the date of manufacture at room temperature and a shelf life of about 90 days at about 38° C. The PVA coating formulation may normally be used at 38° C. The PVA coating formulation may be heated to its application temperature, with mixing, for 24 hours before use ensuring that all components are in solution and well mixed. The PVA coating formulation may be screened through the 20×20 stainless steel screen before being stored or used for dipping or spray or other coating processes.

Example 4

Coating Formulation for Spray Coating

A liter of coating formulation comprising AgSD (30.0 g), PVA (41.7 g, MW=31,000 to 50,000, 87-89% hydrolysis), PVA (16.7 g, MW=89,000 to 98,000, 99+% hydrolysis) and $TiO_2$ (2.0 g) was prepared in accordance with the following procedure.

In an appropriate sized temperature controlled mixing vessel set at moderate mixing, Nitric acid (64 mL, 70%) was added to purified $H_2O$ and diluted to 800 mL. The temperature of the circulating heater with oil & pump was set between 65° C. and 70° C. The variable speed overhead mixer with dissolving stirrer attachment was set at 500 rpm. AgSD 30.0 g was added slowly to the mixing water and acid mixture. The solution was mixed for a minimum of 3 hours. The dissolution was confirmed by turning off the mixer and observing that no solid particles settle out after 60 seconds. The temperature of the circulating heater was set to 80° C. and the stirrer was turned back on. The temperature in temperature controlled vessel containing the drug/acid mixture was allowed to reach at least 75° C. before proceeding.

Micronized Titanium dioxide (2.0 g) was added to 58.4 g of dry PVA powder. The two powders are well mixed with each other, before being added together to the AgSD solution. While maintaining the temperature between 75° C. and 80° C., the PVA Titanium Dioxide mixture was added to the acid/water AgSD solution with stirring at 500 rpm. The solution was mixed for an additional 3 hours at 500 rpm. The resulting PVA coating formulation was a light yellow color and had a smooth appearance in about an hour after the last component was added. The final volume was brought to 1.0 L with purified water.

The PVA coating formulation may be stored at room temperate in a covered/sealed container until use. The PVA coating formulation may have a shelf life of about 5 days from the date of manufacture at room temperature and a shelf life of about 90 days at about 38° C. The PVA coating formulation may normally be used at 38° C. The PVA coating formulation may be heated to its application temperature, with mixing, for 24 hours before use ensuring that all components are in solution and well mixed. The PVA coating formulation may be screened through the 20×20 stainless steel screen before being stored or used for dipping or spray or other coating processes.

Example 5

Cross-Linking Formulation

A liter of cross-linking solution is prepared by measuring 867 mL of purified water and adding while stirring: 27 mL 37% HCl. The solution is stirred for a minimum of 3 minutes before proceeding. Next, 25 mL 40% glyoxal, and 81 mL 37% formaldehyde are added sequentially, with 3 minutes of stirring after each addition. Cross-linker is stored at room temperature in a covered container until it is used. The shelf-life is 90 days from the date of manufacture.

Example 6

Coating Method

A catheter to be coated was dipped into the coating material at a temperature of approximately 38° C. for 30 seconds. The catheter was spun at 2 rpm during the immersion. The catheter was then mechanically withdrawn from the coating material at a speed that varied from 5 to 7 mm/second, while spinning the part at 5 rpm. The catheter was then dried for 10 minutes at 83° F., and followed by a cross-linking step. The cross-linking step consists of submerging the coated and dried catheter into a solution containing the cross-linking formulation for 40 seconds, while spinning at 5 rpm. The catheter is removed from the cross-linking solution at 25 mm/sec and 5 rpm. Additional drying of 10 minutes at 83° F. allows removal of excess crosslinking agent, and ensures consistent coatings.

Example 7

Multiple Coating Method

The catheter of Example 4 was dipped into the coating mixture twice, and a cross-linking solution once at the end of the cycle. During coating, the first dip sat in the coating for 30 seconds to allow the temperature of the catheter to equilibrate with the coating. It was withdrawn through the drying plenum, and held for about 60 seconds before dipping a second time. The catheter was completely submerged for 5 seconds before beginning withdrawal through the drying plenum. Following a drying step, the coated catheter was then combined with a solution containing a crosslinking agent as above.

Example 8

Coating Pretreatment Method

A catheter was pretreated prior to coating. Contaminants on the surface of the catheter, such as oil and mold release agents, were removed by pumping down the pressure to 25 mTorr. The oxygen cleaning and etching step was performed by setting the power of a plasma apparatus at 495 Watts and increasing the pressure to 120 mTorr. The allyl alcohol functionalization step was performed using a flow rate=0.25 mL of alcohol/mm for 8 minutes with 3% argon as a carrier gas at a pressure of approximately 50 mTorr. The allyl alcohol addition can also be done with 3% argon and 5% oxygen as the carrier gases.

The presence of alcohol functional groups on the pretreated catheter, was detected by soaking the sample in a solution containing a fluorescent probe, such as 5-(4,6-dichlorotrazinyl)aminofluoroscein (DTAF) overnight and a using a fluorometer to detect the DTAF signal on the surface of the catheter. The presence of alcohol functional groups was alternatively detected by dipping the catheter into 10 mg/L methylene blue solution for 5 minutes. Samples with alcohol groups on the surface come out medium blue, while those without the turn out only slightly blue.

Example 9

Cross-Linking Procedure

The coating was cross-linked using a dip process which is carried out using similar tank, mixing conditions, temperature control and drying systems as described in Examples 4 and 5. The catheter was dipped for 40 seconds into a tank containing a cross-linking agent (1% glyoxal, 3% formaldehyde, 1% HCl) and withdrawn at 25 mm/sec through the drying plenum with airflow at several liters/mm and a temperature of 70° C.

Example 10

Measurement of Coating Thickness & Estimation of AgSD Concentration

Coating thickness was measured using standard techniques. The catheter was cut using a scalpel forming a cross-sectional segment having a thickness of to about 1 mm. The coating thickness was measured utilizing an optical microscope using standard techniques.

Loading calculations were based on the percent loading rate (wet=2%) and loss on drying (~70%). The total loading therefore increases to 6.7% by weight. The weight of the catheter was measured before and after the application of the coating, and the total mass of dried coating was multiplied by 6.7% to obtain the total AgSD concentration. An analogous procedure was used for $TiO_2$. $TiO_2$ was estimated to be 0.2% by weight wet.

Example 11

Dynamic Biofilm Assay

The bacterial inoculum level was maintained at a consistent level. The inoculum was obtained by serially diluting an overnight batch of bacterial culture of an appropriate organism. These serially diluted batch cultures were then used to inoculate syringes containing an appropriate diluent. Inoculum controls were monitored daily to maintain uniform bacterial concentrations for coated material sections. Controls were prepared in duplicate and were plated at t=0 hours and t=24 hours.

A protein soak was performed prior to contacting the coated material with the inoculum for the purposes of mediating bacterial attachment. The protein soak was typically performed for a time period of about 5 minutes utilizing either human urine or serum. Following the protein soak, the coated material was transferred to a flow cell and the inoculated syringes were placed onto syringe pumps and attached to the flow cells. Length measurements were calculated to correspond to an overall surface area of 100 $mm^2$. Throughout the duration of the assay, the flow of inoculum was maintained at a constant flow rate (0.007 mL/min).

At 24 hour intervals, a sample of the coated material was removed from its flow cell and rinsed by immersing the coated material 10 times each in 4 subsequent rinse stations, which contained either Phosphate Buffered Saline or Nanopure Water, thereby removing planktonic cells and leaving only adhered bacterial cells. Following the rinse, the coated material was transferred into an appropriate neutralizing solution, which was specific to the coated materials' anti-infective coating.

The coated material and neutralizing solution were then aseptically transferred to a sterile petri dish, wherein the biofilm was removed from the coated material utilizing a sterile scalpel. The neutralizing solution and biofilm were passed through a pipette tip approximately 10 times to break up the biofilm. The coated material and neutralizing solution containing the biofilm were then transferred into a test tube and pulse sonicated for 30 seconds, thereby breaking up any remaining large groups of biofilm. Following the sonication, the biofilm was evenly distributed in the neutralizing solution by subjecting the test tube to vortex (30 seconds). The biofilm/neutralizing solution was serially diluted, followed by drop plate enumeration of the dilutions.

Example 12

Static Biofilm Assay

The bacterial inoculum level was maintained at a consistent level. The inoculum was obtained by serially diluting an overnight batch of bacterial culture of an appropriate organism. These serially diluted batch cultures were then used to inoculate test tubes containing an appropriate diluent. Inoculum controls were monitored daily to maintain uniform bacterial concentrations for coated material sections. Controls were prepared in duplicate and were plated at t=0 hours and t=24 hours.

Length measurements of samples to be analyzed were calculated to correspond to an overall surface area of 100 $mm^2$. A protein soak was performed prior to contacting the coated material with inoculum for the purpose of mediating bacterial attachment. The protein soak was typically performed for a time period of about 5 minutes utilizing either human urine or serum. Following the protein soak, the coated material was then transferred to a sterile vile containing an appropriate diluent, which had been inoculated with desired concentration of the microbial organism.

Test tubes containing the coated material were placed onto test tube rockers for 24 hours. Following the designated number of 24 hour contact cycles, the coated material to be processed was removed from the system. Coated materials that were to continue to endure bacterial contact were kept separate from the samples used for quantifying adhesion. Each remaining test tube was additionally inoculated with the microbial organism at 24 hour intervals.

The coated material was rinsed by immersing the coated material 10 times each in 4 subsequent rinse solutions comprising either Phosphate Buffered Saline or Nanopure Water, facilitating the removal of planktonic cells and leaving only adhered bacterial cells. Following the rinse, the coated material was transferred into an appropriate neutralizing solution.

The coated material and neutralizing solution were then aseptically transferred to a sterile petri dish, wherein the biofilm was removed utilizing a sterile scalpel. The neutralizing solution and biofilm were passed through a pipette tip approximately 10 times to break up the biofilm.

The coated material and neutralizing solution containing the biofilm were then transferred into a test tube and pulse sonicated for 30 seconds, thereby breaking up any remaining large groups of biofilm. Following the sonication, the biofilm was evenly distributed in the neutralizing solution by subjecting the test tube to vortex (30 seconds). The biofilm/neutralizing solution was serially diluted and was followed by drop plate enumeration of the dilutions All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

Example 13

Spray Coating Process

A PVA based spray coating was applied to polycarbonate needle-less connectors. The PVA material used consisted of that prepared as in Example 4, above. Two separate ultrasonic sprayers were utilized to atomize the PVA material and the cross-linking solutions. A rotary part holder was used to sequentially move the parts through a series of spray and cross-linking cycles consisting of: coating spray 16 μL, 7.5 Watts, 5 seconds of spray; 3 minutes of drying at 80° F.; cross-linking spray 16 μL, 4.0 Watts, 5 seconds of spray; 3 minutes of drying; coating spray 16 μL, 7.5 Watts, 5 seconds of spray; 3 minutes of drying at 80° F.; cross-linking spray 16 μL, 4.0 Watts, 5 seconds of spray; drying time of 5 minutes at 80° F. The spray volumes and times varied based on the surface area of the part to be sprayed, while all other parameters were held constant.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the spirit and scope of the invention encompassed by the appended claims.

What is claimed is:

1. A method of coating a substrate with an antimicrobial coating, the method comprising:
    pre-treating a surface of the substrate with a primer layer or a surface oxidant;
    preparing a solution comprising nitric acid and silver sulfadiazine;
    heating the solution to a temperature between about 65° C. and about 70° C.;
    adding polyvinyl alcohol to the solution to form a coating solution;
    heating the coating solution to a temperature between about 75° C. and about 80° C. to solubilize the silver sulfadiazine in the coating solution;
    depositing a layer of the coating solution containing solubilized silver sulfadiazine on the surface of the substrate;
    crosslinking the polyvinyl alcohol within the layer to form a surface immobilized, three-dimensional hydrogel network on the substrate; and
    at least partially drying the layer, wherein after at least partially drying the layer, the silver sulfadiazine remains solubilized in the layer.

2. The method of claim 1, wherein the solution is stirred at 500 rpm for at least 15 minutes while at a temperature between about 65° C. and about 70° C., and wherein the coating solution is stirred for about 3 hours at a temperature between about 75° C. and about 80° C. to solubilize the silver sulfadiazine in the coating solution.

3. The method of claim 1 wherein pre-treating the surface of the substrate material comprises coating the surface of the substrate material with the primer layer on which the antimicrobial coating is deposited.

4. The method of claim 1 wherein pre-treating the surface of the substrate material with a surface oxidant comprises subjecting the substrate material to an oxidation process that is followed by a chemical grafting reaction rendering the surface hydrophilic, and compatible with the coating.

5. The method of claim 1 wherein the surface oxidant comprises plasma.

6. The method of claim 1 wherein the coating composition further comprises a stabilizing agent.

7. The method of claim 6 wherein the stabilizing agent is an antioxidant selected from the group consisting of lactone, phenolic, phosphite, thioester, hindered amine, hindered benozoate or hindered phenolic, and combinations thereof.

8. The method of claim 6 wherein the stabilizing agent is an antioxidant selected from the group consisting of:
    1,3,5-tris(4-tert-butyl-3-hydroxy-2,6-dimethylbenzyl)-1,3,5-triazine-2,4,6-(1H,3H,5H)-trione; poly-hexamethylene; 3,5-di-t-butyl-4-hydroxybenzoic acid hexadecyl ester; alpha-tocopherol; alpha-tocopherol polyetheylene glycol succinate; alpha-lipoic acid; butylated hydroxy toluene, sodium ascorbate, and combinations thereof.

9. The method of claim 6 wherein the stabilizing agent is a photostabilizer selected from the group consisting of benzoate, benzophenone, benzotriazole, cyanoacrylate, organo nickel or organo zinc.

10. The method of claim 6 wherein the stabilizing agent is selected from the group consisting of $TiO_2$, $WO_3$, magnesium silicate and mixtures thereof.

11. The method of claim 10 wherein the stabilizing agent comprises $TiO_2$.

12. The method of claim 1 further comprising:
    chemically grafting an aliphatic alcohol onto the substrate material.

13. The method of claim 1 wherein the silver sulfadiazine is solubilized in the coating solution at a concentration between 1 mg/L and 100 g/L.

* * * * *